United States Patent [19]

Liversidge et al.

[11] Patent Number: 5,318,767
[45] Date of Patent: Jun. 7, 1994

[54] X-RAY CONTRAST COMPOSITIONS USEFUL IN MEDICAL IMAGING

[75] Inventors: Gary G. Liversidge, West Chester; Eugene R. Cooper, Berwyn; J. Michael Shaw, King of Prussia; Gregory L. McIntire, West Chester, all of Pa.

[73] Assignee: Sterling Winthrop Inc., New York, N.Y.

[21] Appl. No.: 928,244

[22] Filed: Aug. 10, 1992

Related U.S. Application Data

[63] Continuation-in-part of Ser. No. 647,105, Jan. 25, 1991, Pat. No. 5,145,684, and a continuation-in-part of Ser. No. 810,261, Dec. 19, 1991, abandoned.

[51] Int. Cl.$^5$ .............................................. A61K 49/04
[52] U.S. Cl. ........................................ 424/4; 424/5; 424/489
[58] Field of Search ............................ 424/5, 4, 9, 499

[56] References Cited

U.S. PATENT DOCUMENTS

| | | | |
|---|---|---|---|
| 2,996,433 | 8/1961 | Hoppe et al | 167/95 |
| 3,192,118 | 6/1965 | Battista et al. | 167/95 |
| 4,225,581 | 9/1980 | Kreuter et al. | 424/19 |
| 4,269,821 | 5/1981 | Kreuter et al. | 424/19 |
| 4,540,602 | 9/1985 | Motoyama et al. | 427/213.31 |
| 4,826,689 | 5/1989 | Violante et al. | 424/489 |
| 5,019,370 | 5/1991 | Jay et al. | 424/4 |
| 5,075,502 | 12/1991 | Kneller et al. | 424/5 |
| 5,091,188 | 2/1992 | Haynes | 424/450 |
| 5,141,739 | 8/1992 | Jung et al. | 424/5 |
| 5,145,684 | 9/1992 | Liversidge et al. | 424/499 |

FOREIGN PATENT DOCUMENTS

| | | |
|---|---|---|
| 0498482A2 | 1/1992 | European Pat. Off. . |
| 492482 | 8/1992 | European Pat. Off. . |
| 9007491 | 7/1990 | PCT Int'l Appl. . |
| 9014846 | 12/1990 | PCT Int'l Appl. . |

OTHER PUBLICATIONS

Violante et al., Particulate Contrast Media, 1980, Investigative Radiology, 15:5329–5334.
Lauteala et al., Response of White Blood Cells to Iodipamide Ethyl Ester Particles 1986, Investigative Radiology, 21:562–565.
Violante et al., Particulate Suspensions as Contrast Media, 1984, Radiocontrast Agents, 73:543–576.

Primary Examiner—Thurman K. Page
Assistant Examiner—W. Benston
Attorney, Agent, or Firm—William J. Davis

[57] ABSTRACT

An X-ray contrast composition comprising particles consisting essentially of a non-radioactive crystalline organic x-ray contrast agent having a surface modifier adsorbed on the surface thereof in an amount sufficient to maintain an effective average particle size of less than 400 nm, and a pharmaceutically acceptable carrier therefor is useful in x-ray diagnostic medical imaging methods. The agents can be delivered to a specific tissue or fluid site, for example, the blood pool, liver or spleen. In one embodiment involving intravenous administration, preferred compositions provide effective imaging of the blood pool for remarkably long times.

28 Claims, No Drawings

X-RAY CONTRAST COMPOSITIONS USEFUL IN MEDICAL IMAGING

CROSS REFERENCE TO RELATED APPLICATIONS

This application is a continuation-in-part of U.S. patent application Ser. No. 647,105, filed Jan. 25, 1991, now U.S. Pat. No. 5,145,684, and U.S. patent application Ser. No. 810,261, filed Dec. 19, 1991 now abandoned, the disclosures of which are hereby incorporated by reference.

FIELD OF INVENTION

This invention relates to x-ray contrast compositions for medical x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on contrast agents and media in medical imaging is provided by D. P. Swanson et al, *Pharmaceuticals in Medical Imaging*, 1990, MacMillan Publishing Company, the disclosure of which is hereby incorporated by reference in its entirety.

Briefly, in x-ray imaging, transmitted radiation is used to produce a radiograph based upon overall tissue attenuation characteristics. X-rays pass through various tissues and are attenuated by scattering, i.e., reflection or refraction or energy absorption. However, certain body organs, vessels and anatomical sites exhibit so little absorption of x-ray radiation that radiographs of these body portions are difficult to obtain. To overcome this problem, radiologists routinely introduce an x-ray absorbing medium containing a contrast agent into such body organs, vessels and anatomical sites.

Currently available X-ray contrast agents generally exhibit a lack of site directed delivery or compartmentalization. Consequently, large quantities of agent are normally required for imaging. It would be desirable to restrict the contrast agent to specific biological or anatomical compartments, such as the blood pool, liver, kidney or spleen. This would reduce the overall amount of agent which needs to be administered to achieve the desired contrast enhancement.

Maximum enhancement of major blood vessels takes place during the so-called vascular phase of contrast media kinetics which occurs within about the first two minutes following the intravascular infusion or bolus injection of the contrast media. This is because the plasma concentration of an intravascular contrast medium decreases rapidly as a result of vascular mixing, transcapillary diffusion of the medium from the circulation into the interstitial spaces and renal excretion. Consequently, imaging of blood vessels must take place within a narrow time window, typically within a few minutes after infusion or injection of the x-ray contrast agent. Currently, there is no commercially available x-ray contrast agent for imaging blood vessels which provides good contrast images of the vasculature for an extended period of time. Therefore, multiple injections are often required to visualize the vasculature adequately. Furthermore, arteriography, as currently practiced, typically requires percutaneous or surgical catheterization, fluoroscopic localization and multiple bolus arterial administrations to adequately visualize a given vascular region.

The need for improved visualization of the liver, kidney and spleen, particularly for early detection of metastases, has led to numerous attempts at developing a contrast medium for accumulation by the mononuclear phagocyte system (MPS). In *Handbook of Experimental Pharmacology*, Vol. 73, Radiocontrast Agents, Chapter 13, "Particulate Suspensions as Contrast Media", Violante and Fischer describe and analyze the problems and complexities involved in designing and formulating such a medium. Inasmuch as the MPS of the liver and spleen is known to trap particles by phagocytosis, contrast agents in particulate form, such as emulsions of iodinated oils, e.g., iodinated ethyl esters of poppy seed oil, and liposomes containing water soluble iodinated contrast agents have been proposed for liver and spleen visualization. However, emulsions tend to be unacceptably toxic when administered both intravenously and subcutaneously and liposomes tend to require unacceptably large amounts of lipid to achieve adequate contrast enhancement. The MPS or Kuppfer cells of the liver, to which liposomes and emulsions have been directed, constitute approximately 5 percent of the total cell population, the remainder being hepatocyte cells.

Submicron inorganic radioactive thorium dioxide particles have been used for liver visualization and have shown effective contrast enhancement in clinical testing. However, their use has been discontinued because of the extremely lengthy retention of the particles in the liver. This, in combination with the inherent radioactivity of thorium, has led to serious adverse side effects including neoplasm and fibrosis.

Violante et al, U.S. Pat. No. 4,826,689, disclose a method of making uniformly sized noncrystalline amorphous particles from water-insoluble organic compounds wherein the organic compound is dissolved in an organic solvent. In one embodiment, iodipamide ethyl ester is dissolved in dimethyl sulfoxide. However, solvent precipitation techniques such as described in U.S. Pat. No. 4,826,689 for preparing particles tend to provide solvent contaminated particles. Such solvents are often toxic and can be very difficult, if not impossible, to adequately remove to pharmaceutically acceptable levels for diagnostic imaging. Additionally, amorphous materials and formulations tend to exhibit unacceptably poor stability and/or short shelf-lives.

Motoyama et al, U.S. Pat. No. 4,540,602 disclose that a solid drug can be pulverized in an aqueous solution of a water-soluble high molecular substance, and that as a result of such wet grinding, the drug is formed into finely divided particles ranging from 0.5 $\mu$m or less to 5 $\mu$m in diameter. However, there is no suggestion that particles having an average particle size of less than about 400 nm can be obtained. Indeed, attempts to reproduce the wet grinding procedures described by Motoyama et al resulted in particles having an average particle size of much greater than 1 $\mu$m.

PCT/EP90/00053 describes water insoluble iodinated carbonate esters reported to be useful as contrast agents for visualization of the liver and spleen. Particles of mean diameter on the order of 1.0 micron of the disclosed esters reportedly are taken up by the reticuloendothelial system of the liver and spleen. However, such particles are prepared by conventional mechanical crushing or spray drying techniques or by solvent precipitation techniques such as described in U.S. Pat. No. 4,826,689.

Currently, there is no completely satisfactory x-ray contrast agent in the market for liver and spleen imaging. Each contrast agent and/or composition proposed for liver and spleen imaging has some disadvantage.

It would be desirable to provide improved x-ray contrast compositions for imaging vessels, anatomical sites and body organs such as the liver and spleen. Moreover, it would be highly desirable to provide intravenously administered x-ray contrast compositions which demonstrate effective imaging of the blood pool for extended periods of time.

SUMMARY OF THE INVENTION

We have discovered that surface modified crystalline nanoparticles of water-insoluble x-ray contrast agents provide images of exceptional resolution and can be formulated for enhanced delivery to specific tissue or fluid sites, e.g., the blood pool, liver, kidney, bone marrow, lymph nodes and spleen. Moreover, preferred x-ray contrast agents when administered intravenously provide effective imaging of the blood pool within the vascular system for remarkably long periods of time.

More particularly, in accordance with this invention, there is provided an x-ray contrast composition comprising particles consisting essentially of a non-radioactive crystalline organic x-ray contrast agent having a surface modifier adsorbed on the surface thereof in an amount sufficient to maintain an effective average particle size of less than 400 nm, and a pharmaceutically acceptable carrier therefor.

In accordance with this invention there is also provided a method for x-ray diagnostic imaging which comprises administering to the body of a test subject an effective contrast producing amount of the above-described x-ray contrast composition.

This invention further provides a method for the preparation of the above described x-ray contrast composition which includes the steps of introducing a non-radioactive organic x-ray contrast agent, a liquid medium, grinding media, and optionally a surface modifier into a grinding vessel; wet grinding the contrast agent and thereafter mixing a surface modifier with the liquid medium if the surface modifier was not present during grinding to form particles having an average size of less than about 400 nm; and separating the particles from the grinding vessel and media.

It is an advantageous feature of this invention that x-ray contrast compositions are provided which demonstrate effective imaging of the blood pool within the vascular system for unexpectedly long periods of time, e.g., up to 2 hours and longer.

It is another advantageous feature of this invention that x-ray contrast compositions are provided with enhanced delivery to specific anatomical sites, e.g., the blood pool within the vascular system, liver, kidney, bone marrow, lymph nodes or spleen. This enables enhanced imaging of the site with reduced amounts of agent.

It is another advantageous feature of this invention that intravenous injectable x-ray contrast compositions are provided which do not require catheterization during angiography.

Still another advantageous feature of this invention is that x-ray contrast compositions are provided which can be formulated with high loadings of existing x-ray contrast agents and/or derivatives thereof.

Yet another advantageous feature is that desired levels of contrast, as determined by a particular iodine content, can be achieved with lesser amounts of the x-ray contrast compositions of this invention as compared to prior art compositions containing conventional, e.g., polymeric carriers.

Other advantageous features will become readily apparent upon reference to the following description of preferred embodiments.

DESCRIPTION OF PREFERRED EMBODIMENTS

The x-ray contrast composition of this invention comprises particles of an organic x-ray contrast agent having a surface modifier adsorbed on the surface thereof in an amount sufficient to maintain an effective average particle size of less than 400 nm. Such particles comprising ethyl-3,5-diacetoamido-2,4,6-triiodobenzoate are disclosed in U.S. Patent application Ser. No. 647,105 cited above. In addition, U.S. patent application Ser. No. 647,105 generically discloses surface modified drug nanoparticles, having an effective average particle size of less than about 400 nm, consisting of a crystalline drug substance having a surface modifier adsorbed on the surface thereof, and a method for the preparation of such particles. Pharmaceutical compositions containing such particles exhibit outstanding clinical utility and are believed to possess substantial commercial value.

The x-ray contrast agent useful in the practice of this invention is non-radioactive and exists as a discrete, crystalline phase of an organic substance. The crystalline phase differs from an amorphous or non-crystalline phase which results from solvent precipitation techniques such as described in U.S. Pat. No. 4,826,689 noted above. The organic substance can be present in one or more suitable crystalline phases. The invention can be practiced with a wide variety of crystalline, non-radioactive x-ray contrast agents. However, the x-ray contrast agent must be poorly soluble and dispersible in at least one liquid medium. By "poorly soluble", it is meant that the agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media in which the selected x-ray contrast agent is poorly soluble and dispersible, including, for example, aqueous saline solutions, such as phosphate buffered saline (PBS), plasma, mixed aqueous and nonaqueous solutions, for example, water and alcohol, and suitable nonaqueous solvents such as alcohol, glycerol and the like.

The x-ray contrast agent can be an iodinated compound. The iodinated compound can be aromatic or nonaromatic. Aromatic compounds are preferred. The iodinated compound can comprise, one, two, three or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido, butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic acid, iothalamic acid, trimesic acid, ioxaglic acid (hexabrix), ioxitalamic acid, tetraiodoterephthalic acid, and the like. It is contemplated that poorly soluble derivatives of iodamide and iopyrol can be used herein.

The invention can also be practiced with poorly soluble derivatives, e.g., ester and ether derivatives, of hydroxylated nonionic x-ray contrast agents. Illustrative nonionic contrast agents include, but are not limited to, metrizamide; ioglunide; iopamidol; iopromide; iogulamide; iohexol, and other compounds described in U.S. Pat. No. 4,250,113; Ioversol, and other compounds described in U.S. Pat. No. 4,396,598; nonionic triiodinated compounds, such as described in Investigative Radiology, Vol. 19, July-August 1984; and nonionic dimers, such as described in Radiology, 142: 115-118, January 1982. The invention can be practiced with poorly soluble derivatives of iodomethane sulfonamides, iodinated aromatic glucoanilides, 2-ketogulonamides, reversed amides, peptides, carbamates, esters, glycoside and glucose derivatives, benzamide derivatives, isophthalamides, bis compounds, and bispolyhydroxylated acylamides, such as described in Volume 73 of the Handbook of Experimental Pharmacology, entitled Radiocontrast Agents, edited by M. Sovak, 1984, Springer-Verlag, Berlin, pages 56-73.

Many of the iodinated molecules described above, if in monomeric form, can also be prepared as dimers (sometimes referred to as bis compounds), trimers (sometimes referred to as tris compounds), etc., by techniques known in the art. It is contemplated that this invention can be practiced with poorly soluble-iodinated compounds in monomeric, dimeric, trimeric and polymeric forms. Representative illustrative compounds are described by Sovak, cited above, pages 40-53.

Classes of preferred contrast agents have the following structural formulae:

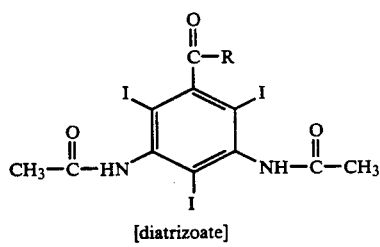

[diatrizoate]

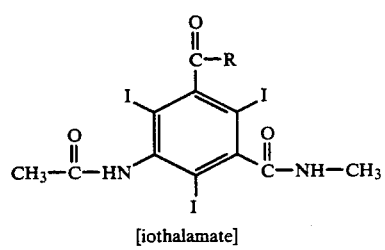

[iothalamate]

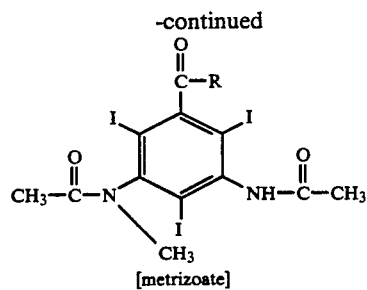

[metrizoate]

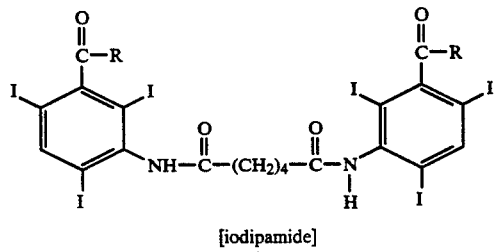

[iodipamide]

In the above structures, R can be OR$^1$,

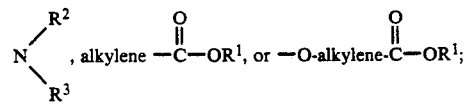

wherein R$^1$ is alkyl, and R$^2$ and R$^3$ are independently H or alkyl. Each alkyl group can independently contain from 1-20, preferably 1-8, and more preferably, 1-4 carbon atoms. The alkylene group preferably contains from 1 to 4 carbon atoms such as methylene, ethylene, propylene and the like.

Particularly preferred contrast agents include the ethyl ester of diatrizoic acid, i.e., ethyl-3,5-diacetamido-2,4,6-triiodobenzoate, also known as ethyl-3,5-bis (acetylamino)-2,4,6-triodobenzoate or ethyl diatrizoate, having the structural formula A above wherein R=—OCH$_2$CH$_3$ (WIN 8883); the ethyl glycolate ester of diatrizoic acid, i.e., ethyl (3, 5-bis (acetylamino) -2,4,6-triiodobenzoyloxy) acetate, also known as ethyl diatrizoxyacetate, having the structural formula A above wherein

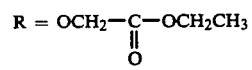

(WIN 12901); and ethyl-2-(3,5-bis(acetylamino) -2,4,6-triiodobenzoyloxy)butyrate, also known as ethyl-2-diatrizoxybutyrate (WIN 16318).

In addition, it is expected that the invention can be practiced in conjunction with the water insoluble iodinated carbonate esters described in PCT/EP90/00053.

The above described x-ray contrast agents are known compounds and/or can be prepared by techniques known in the art. For example, water-insoluble esters and terminal amides of acids such as the above-described iodinated aromatic acids can be prepared by conventional alkylation or amidation techniques known in the art. The above-noted acids and other acids which can be used as starting materials are commercially available and/or can be prepared by techniques known in the art. The examples which follow contain illustrative examples of known synthetic techniques.

The particles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants. Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986, the disclosure of which is hereby incorporated by reference in its entirety.

Particularly preferred surface modifiers include polyvinylpyrrolidone, tyloxapol, poloxamers such as Pluronic F68 and F108, which are block copolymers of ethylene oxide and propylene oxide, and poloxamines such as Tetronic 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have been found to be particularly useful include Tetronic 908, the Tweens, Pluronic F-68 and polyvinylpyrrolidone. Other useful surface modifiers include:
decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glucopyranoside;
octanoyl-N-methylglucamide;
n-octyl β-D-glucopyranoside;
octyl β-D-thioglucopyranoside;
and the like.

A particularly preferred class of surface modifiers includes water-soluble or water-dispersible compounds having the formula

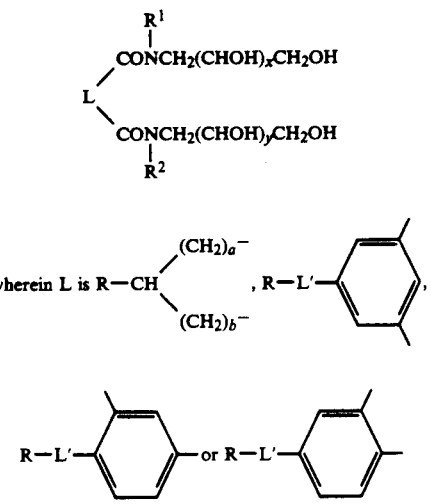

L' is a chemical bond, —O—, —S—, —NH—, —CONH— or —SO₂NH—;

R is a hydrophobic substituted or unsubstituted alkyl, substituted or unsubstituted cycloalkyl, or a substituted or unsubstituted aryl group;

each of R¹ and R² independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

Preferred compounds within this class conform to the above structure wherein R contains from 6 to 36 carbon atoms, for example, R is an n-alkyl group containing from 6 to 18 carbon atoms, each of R¹ and R² independently is a methyl, ethyl, propyl or butyl group and a is 0 and b is 0. This class of surface modifiers is described in U.K. Patent Application No. 9104957.7 filed Mar. 8, 1991 and can be prepared by reacting an appropriate dicarboxylic acid ester with an appropriate monosaccharide amine, preferably in the absence of a solvent, at a reaction temperature from 140° to 200° C.

The surface modifiers are commercially available and/or can be prepared by techniques known in the art. Two or more surface modifiers can be used in combination.

The particles useful in the practice of this invention can be prepared in accordance with the wet grinding process described in U.S. patent application Ser. No. 647,105 referenced above. The process comprises dispersing a poorly soluble x-ray contrast agent in a liquid dispersion medium and wet-grinding the agent in the presence of grinding media to reduce the particle size of the contrast agent to an effective average particle size of less than about 400 nm. The particles can be reduced in size in the presence of a surface modifier. Alternatively, the particles can be contacted with a surface modifier after attrition.

A general procedure for preparing the particles useful in the practice of this invention follows. The x-ray contrast agent selected is obtained commercially and/or prepared by techniques known in the art as described above, in a conventional coarse form. It is preferred, but not essential, that the particle size of the coarse x-ray contrast agent selected be less than about 100 μm as determined by sieve analysis. If the coarse particle size of the contrast agent is greater than about 100 μm, then it is preferred that the coarse particles of the contrast agent be reduced in size to less than 100 μm using a conventional milling method such as airjet or fragmentation milling.

The coarse imaging agent selected can then be added to a liquid medium in which it is essentially insoluble to form a premix. The concentration of the agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 20–60%, by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the drug substance and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to Afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. We have found that zirconium oxide, such as 95% ZrO stabilized with magnesia, zirconium silicate, and glass grinding media provide particles having levels of contamination which are believed to be acceptable for the preparation of x-ray contrast compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the imaging agent. Processing temperatures of less than about 30–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of imaging agent and surface modifier can vary widely and the optimal amount of the surface modifier can depend, for example, upon the particular imaging agent and surface modifier selected, the critical micelle concentration of the surface modifier if it forms micelies, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the imaging agent. The surface modifier can be present in an amount of 0.1–90%, preferably 10–60%, more preferably 10–30% by weight based on the total weight of the dry particle.

The applicants have developed a simple screening process whereby compatible surface modifiers and imaging agents can be selected which provide stable dispersions of the desired particles. First, coarse particles of an imaging agent of interest are dispersed in a liquid in which the agent is essentially insoluble, e.g., water at 5% (w/v) and milled for 60 minutes in a DYNO-MILL (MODEL KDL, available from Willy A. Bachoffen AG Maschinenfabrik) under the following milling conditions:

Grinding vessel: water jacketed stainless steel chamber
Premix flow rate: 250 ml/min
Available volume of grinding vessel: 555 ml
Media volume: 472 ml
Media type: 0.5–0.75 mm unleaded silica glass beads (distributed by Glen Mills, Inc.)
Recirculation time: 240 min
Residence time: 60 min
Impeller speed: 3000 RPM; tangential speed 1952 ft/min (595 m/min)
Grinding vessel coolant: water
Coolant temperature: 50° F. (10° C.)

The milled material is then divided into aliquots and surface modifiers are added at concentrations of 2, 10 and 50% by weight based on the total combined weight of the imaging agent and surface modifier. The dispersions are then sonicated (1 minute, 20 kHz) to disperse agglomerates and subjected to particle size analysis by examination under an optical microscope (1000×magnification). If a stable dispersion is observed, then the process for preparing the particular imaging agent surface modifier combination can be optimized in accordance with the teachings above. By stable it is meant that the dispersion exhibits no flocculation or particle agglomeration visible to the naked eye at least 15 minutes, and preferably, at least two days or longer after preparation. In addition, preferred particles exhibit no flocculation or agglomeration when dispersed in at least one or more of the following: PBS, simulated GI fluids, and plasma.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

As indicated in the examples which follow, the x-ray contrast composition of this invention comprising particles consisting of crystalline ethyl-3,5-diacetoamido-2,4,6-triiodobenzoate having Tetronic-908 adsorbed on the surface thereof (average particle size 166 and 188 nm) was particularly useful in imaging the blood pool and spleen. An x-ray contrast composition comprising particles consisting of crystals of the ethyl glycolate ester of diatrizoic acid having Tetronic-908 adsorbed on the surface thereof (average particle size 238 nm) was particularly useful in imaging the liver. Effective imaging of the lymph nodes has been achieved using x-ray contrast compositions comprising particles ranging in size from 170–315 nm consisting of crystalline ethyl-3,5-diacetoamido-2,4,6-triiodobenzoate having Tetronic-908 adsorbed on the surface thereof.

It is not completely understood why stable nonagglomerating dispersions of the above-described fine particles can be provided in narrow particle size distributions by the wet grinding technique according to this invention. While applicants do not wish to be bound by theoretical mechanisms, for intravenous administration it is postulated that the average particle size in conjunction with the imaging agent, the surface modifier selected, and the degree to which the surface modifier remains adsorbed to the particle, affect whether the agent remains in the blood pool or is targeted to a specific site, e.g., taken up by the MPS. It is believed that certain smaller particles, e.g., certain particles having an average particle size less than about 200 nm, are preferentially inclined to recirculate in the blood pool. Larger particles are believed to be preferentially taken up by the MPS of the liver, spleen and bone marrow.

The x-ray contrast compositions of this invention comprise the above-described particles and a carrier therefor. For example, the particles can be dispersed in an aqueous liquid which serves as the carrier for the x-ray contrast agent. Other suitable carriers include liquid carriers such as mixed aqueous and nonaqueous solvents, for example water and alcohols, and suitable nonaqueous solvents, such as alcohol; gels; gases, such as air; and powders. The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

A method for the preparation of an x-ray contrast composition according to this invention includes the steps of introducing a non-radioactive x-ray contrast agent, a liquid medium, grinding media, and optionally, a surface modifier into a grinding vessel; wet grinding to reduce the particle size of the contrast agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the x-ray contrast composition preferably is subjected to a sterilization process. Sterilization can take place in the presence of polyethylene glycols, e.g., PEG 400, available from J. T. Baker Chemical Co., sodium dodecyl sulfate, and/or caprylic acid, which may minimize particle size growth during sterilization.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mgI/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of the tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to the preferred applications discussed above, i.e., for blood pool, liver, spleen and lymph node imaging, the x-ray contrast compositions of this invention are also expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The present invention provides significant advantages compared to compositions prepared by solvent precipitation techniques, such as described by Violante et al in U.S. Pat. No. 4,826,689, which result in the formation of non-crystalline, solvent-contaminated particles. As noted, such solvents are often toxic and can be very difficult, if not impossible, to adequately remove to pharmaceutically acceptable levels to be practical. Solvent removal to pharmaceutically acceptable levels often is of such prohibitive cost so as to be unacceptable from a commercial standpoint. Violante et al teach that the chemical precipitation procedure for providing particles was developed to avoid the problems of obtaining uniform particles of water-insoluble radiopaque contrast materials by conventional techniques. Indeed, the patent teaches away from the present invention by suggesting that physical methods for modifying and controlling particle size are problematic, i.e., result in preparations with unacceptably broad ranges of particle diameters and toxicity.

In addition, as compared with liposomes and emulsions, x-ray compositions according to the invention containing particulate contrast agents have a much higher iodine content. To achieve a desired level of contrast, as provided by a particular amount of iodine, a smaller amount of material can be used. Moreover, x-ray compositions according to this invention are generally more storage stable than prior art lipid and amorphous compositions.

The following examples further illustrate the invention.

EXAMPLE 1

Synthesis of WIN 8883

Ethyl 3,5-diacetoamido-2,4,6-triiodobenzoate

To 8.11 L of dry N,N-dimethylformamide was added 1.01 kg (1.65 mol) of diatrizoic acid. To the vigorously stirred suspension was carefully added 274 g (1.99 mol) of milled potassium carbonate. During the addition there was significant gas evolution. Before all of the suspended solid had gone into solution, a second solid began to form toward the end of the carbonate addition. The mixture was stirred for 30 min. at room temperature. Ethyl iodide (608 g, 3.90 mol) was added dropwise and the mixture was stirred overnight at room temperature at which point the reaction mixture was nearly homogeneous. The reaction was poured into 25 L of water, filtered and the solid washed with water and dried at reduced pressure at 60°C. to afford 962 g (91% yield) of a white solid, mp 280°–290°C. (dec.). Analysis for $C_{13}H_{13}I_3N_2O_4$ calc'd/found: C 24.32/24.27; H 2.05/1.93; N 4.36/4.28.

Preparation of Nanocrystalline Formulation of WIN 8883

A nanoparticle formulation of WIN 8883 was prepared by placing 12.0 g of WIN 8883, 2.0 g of Tetronic 908 surfactant (BASF), and 100 ml of 1 mm ZrO beads (Zircoa, Inc.) into a 200 ml glass bottle having a wide mouth (Qorpak). The ZrO beads were pretreated by rolling in deionized water at 115 rpm for 24 hours followed by rolling in 1M $H_2SO_4$ for 1 hour, rinsed with copious amounts of distilled water and air dried. 60 ml of deionized water was added and the mixture was then rolled on a U.S. Stoneware jar mill (model #784CVM) for 14 days at 115 rpm. At the end of that time, the suspension of particulates was removed from the 1 mm ZrO media by suction and/or filtration (see below) and placed into a brown 120 ml capacity glass bottle. This suspension was then coarse filtered throughout a series of filters (10 micron, 5 micron, 3 micron pore sizes) under gravity (Nucleopore "polycarbonate" filters, Microstar, Inc.) into sterile plastic tubes (Kimble, flat topped, graduated).

Characterization of Properties of Nanocrystalline Formulation of WIN 8883

A suspension of WIN 8883 prepared as described above was characterized for particle size and zeta potential using a Malvern Zeta Sizer III instrument (Malvern Instruments, Ltd.). A small aliquot of suspension was added to approximately 20 ml of 25 mM phosphate buffer at pH=7.0 for analysis. This diluted sample was then introduced into the light scattering cell for analysis by photon correlation spectroscopy. Size is reported as an intensity weighted value and was found to be an average of 166 nm in diameter with a zeta potential of $-2.3$ mV. The particle size distribution was surprisingly narrow.

These samples were further studied for physical stability upon exposure to simulated gastric fluid (i.e., prepared according to USP specifications, containing pepsin, pH adjusted to 2.5 with HCl;), phosphate buffered saline (i.e., a 25 mM sodium phosphate solution containing 0.9% NaCl purchased from Cellgro;), and rat plasma (i.e., plasma obtained from white male Sprague Dawley rats). Microscopic visualization of these samples added to each fluid confirmed no aggregation or flocculation occured.

In Vivo Imaging Studies Using Nanocrystalline WIN 8883; 10%

WIN 8883, 2% Tetronic 908, in water

A suspension of WIN 8883 was prepared as described above except that 6.0 g of WIN 8883 and 1.2 g of T908 were used (i.e., 10% WIN 8883; wt/vol). The suspension was characterized as described above and exhibited an average particle size of 166 nm and a zeta potential of −2.3 mV. Further, the formulation passed all of the fluid stability tests and no adverse effects were noted after injection into mice. This formulation was injected via syringe into the ear vein of approximately 3 kg rabbits for examination of the effect upon computed tomographic (CT) imaging of the rabbit. Imaging was carried out at 5 min. post injection, 30 min. post injection, and 1 hour post injection in the areas of the kidneys, spleen, and liver. Dose was varied from 0.3 ml/kg to 3.0 ml/kg (30 mg/kg to 300 mg/kg) of compound or approximately 16 mg I/kg to 160 mg I/kg which is an important consideration in x-ray contrast enhancement.

The images demonstrated enhanced x-ray density in the blood pool, liver and spleen, especially at 5 min. post injection. This effect in the blood pool was diminished at 30 min. post injection and essentially not discernible at 1 hour post injection. Contrast enhancement within the liver remained essentially constant over this time period. The spleen tended to increase in x-ray density with time. The lowest dose was minimally useful in this manner while the middle dose (i.e., 2 ml/kg or 200 mg/kg) was somewhat efficacious and the highest dose (i.e., 3 ml/kg or 300 mg/kg) was the best at presenting the blood pool.

EXAMPLE 2

In Vivo Imaging Using Nanocrystalline WIN 8883; 20% WIN 8883, 3.3% T908, in water A suspension of WIN 8883 was prepared as described in Example 1 above except that it was milled for 8 days. This suspension was characterized as in Example 1 and exhibited an average size of 180 nm. Stability in the various fluids was determined as described in Example 1. Stability in PBS and rat plasma with slight aggregation in GI fluid was observed.

This formulation was injected via syringe into the ear vein of approximately 3 kg rabbits for examination of the effect upon computed tomographic (CT) imaging of the rabbit. Imaging was carried out at 5 min. post injection, 30 min. post injection, and 1 hour post injection in the areas of the kidneys, spleen, liver, and the chest cavity. Dose was varied (0.5 ml/kg, 1.0 ml/kg, 1.5 ml/kg), (100 mg/kg, 200 mg/kg, and 300 mg/kg of compound) (59 mg I/kg, 118 mg I/kg, and 176 mg I/kg) respectively.

The images demonstrated enhanced x-ray density in the blood pool, liver and spleen, especially at 5 min. post injection. The blood pool enhancement was readily seen in the images of the chest cavity within the chambers of the heart. This effect in the blood pool was greatly diminished at 30 min. post injection and essentially not discernible at 1 hour post injection. Contrast enhancement within the liver remained essentially constant over this time period. The spleen tended to increase in x-ray density with time. These effects were observed at all dose levels with decreasing density with decreasing dose.

Images taken at 7 and 22 days post injection clearly demonstrated diminished x-ray density within the spleen.

EXAMPLE 3

In Vivo Imaging Studies Using Nanocrystalline WIN 8883; 20% WIN 8883, 3.3% T908, in PBS A suspension of WIN 8883 was prepared as described above except that PBS was used instead of water. PBS was used to control pH and achieve approximate equi-osmolality with blood. These particles were characterized as in Example 1 and exhibited an average size of 159 nm and a zeta potential of −3.5 mV. The pH of this suspension was measured as 9.5 while the osmolality was determined to be 249 mOsm/kg. While slight aggregation was observed in GI fluid, addition of this suspension to either PBS or rat plasma did not result in aggregation or flocculation.

This formulation was injected via syringe into the ear vein of approximately 3 kg rabbits for examination of the effect upon computed tomographic (CT) imaging of the rabbit. Imaging was carried out at 5 min. post injection, 30 min. post injection, and 1 hour post injection in the areas of the kidneys, the spleen, the liver, and the chest cavity. Dosages were administered at 0.5 ml/kg, 1.0 ml/kg, and 1.5 ml/kg (100 mg/kg, 200 mg/kg, and 300 mg/kg of compound) (59 mg I/kg, 118 mg I/kg, and 176 mg I/kg) respectively.

The images demonstrated enhanced x-ray density in the blood pool, liver and spleen. The effect in the spleen was not very pronounced at 5 min. post injection, while the blood pool was dramatically enhanced as evidenced by the chambers of the heart and major blood vessels throughout the abdomen and chest cavity. The spleen continued to be enhanced with time (i.e., at 30 min. post injection) while the blood pool remained fairly constant over this time period indicating improved performance (with respect to blood pool imaging) of this formulation over that observed in Examples 1 and 2. The liver intensity remained fairly constant over this time as well. At 1 hour post injection, the liver and blood pool began to fade in density while the spleen remained enhanced. Imaging at 7 days and 22 days post injection showed that the spleen indeed returned to pre-imaging x-ray densities with time.

EXAMPLE 4

In Vivo Imaging Studies Using Nanocrystalline WIN 8883;20% WIN 8883, 3.3% T908, phosphate buffer A suspension of WIN 8883 was prepared as described in Example 1 except that a moderately concentrated phosphate buffer (0.1M, pH=7.5) was used as the solution phase rather than water alone. This resulted in the suspension being at physiologically acceptable pH (i.e., pH=7.5) and osmolality (i.e., 344 mOsm/kg). Further, the milling time was decreased to 22 hours. The suspension was characterized as in Example 1 and resulted in an average particle size of 258 nm.

This formulation was imaged as described in Examples 2 and 3. The images demonstrated very little enhancement of the blood pool with dramatic enhancement of the liver and some enhancement of the spleen and kidney at 5 min. post injection. This represents a significant effect believed to result in part from the particle size of these formulations. No mortality was observed in the rabbits upon injection or during the course of the experiment. Any enhancement that may have been present in the blood pool at 5 min. post injection was absent at 30 min. post injection. Liver enhancement and kidney enhancement remained evident at both 30 min. and 1 hour post injection, although diminished after 1 hour.

EXAMPLE 5

In Vivo Imaging Studies Using Nanocrystalline WIN 8883; 10% WIN 8883, 1% surfactant, 1% Polysorbate 20 (i.e., Tween 20), and 5% mannitol A suspension of WIN 8883 was prepared as described in Example 1 except that only 6 g of WIN 8883 (i.e., 10% WIN 8883) was used and the surfactants used included $C_{18}H_{37}$—$CH_2(CON (CH_3) CH_2 (CHOH)_4C-H_2OH)_2$ having a structure which includes an alkyl chain (tail) and 2 acyclic sugar moities as the hydrophilic portion (i.e., head groups) at 0.6 g/60 ml and a polysorbate 20 (Tween 20) at 0.6 g/60 ml. Further, the solution was made equi-osmolar with blood by adding 5% mannitol to the suspension after the initial milling process was completed. This suspension was characterized as described in Example 1 and resulted in an average particle size of 194 nm. Fluid stability was assessed as described in Example 1 and the suspension was found to be stable in GI, PBS, and rat plasma.

This formulation was imaged as described in Example 1 except that only the middle dose (i.e., 1.5 ml/kg animal) was administered. The images demonstrated enhance liver x-ray contrast with no enhancement of the blood pool at 5 min. post injection, 30 min. post injection or 1 hour post injection. The rabbits showed no adverse effects upon administration of this formulation.

EXAMPLE 6

Synthesis of WIN 12901

Ethyl (3,5-bis(acetylamino) -2,4,6-triiodobenzoyloxy)acetate

To 175 mL of dry N, N-dimethylformamide (DMF) was added 63.6 g (0.100 mol) sodium diatrizoate and 14.7 g (0.120 mol) of ethylchloroacetate and the mixture was heated on a steam bath for 6 hr. The reaction was filtered while hot and the filtrate cooled to room temperature and diluted to 500 ml with water. The mixture was cooled and filtered and the collected solid washed with water. The solid was then dissolved in 350 ml hot DMF, filtered and added to an equal volume of water. The mixture was cooled, filtered, washed with water, and the solid dried at 100° C. overnight to afford 53.0 g (76% yield) of a white powder, mp 269.5-270.5° C. Analysis for $C_{15}H_{15}I_3N_2O_6$ calc'd/found: C 25.73/25.80; H 2.15/2.77; I 54.4/53.8.

In Vivo Imaging Studies Using Nanocrystalline WIN 12901; 10% WIN 12901, 2% T908, in water A suspension of WIN 12901 was prepared as described in Example 1 except that 6 g of WIN 12901 (i.e., 10% WIN 12901) and 1.2 g T908 (i.e., 2% T908) were used. The suspension was milled for 4 days. These particles were characterized as described in Example 1. The average particle size measured was 238 nm. Fluid stability assessment as described in Example 1 suggested stability in GI, PBS, and rat plasma.

This formulation was imaged as described in Example 1. The images demonstrated enhanced blood pool x-ray contrast, liver contrast and kidney contrast at 5 min. post injection, enhanced liver and kidney contrast at 30 min. post injection and somewhat diminished liver and kidney enhancement at 1 hour post injection. The density in the liver was particularly striking.

EXAMPLE 7

In Vivo Imaging Studies Using Nanocrystalline WIN 12901; 20% WIN 12901, 3.3% T908, 100 mM phosphate buffer A suspension of WIN 12901 was prepared as described in Example 1 except that 100 mM phosphate buffer at pH=6.5 was used instead of water. This was used to control the pH and osmolality of this formulation. These particles were characterized as described in Example 1 and exhibited an average size of 289 nm. The pH of the samples was 6.5 and the osmolality 344 mOsm/Kg. Fluid stability was assessed as described in Example 1. This formulation was found to be stable in PBS, GI, and rat plasma.

This formulation was imaged as described in Example 1 except that a dose of 1.5 ml/Kg animal weight was administered. Imaging studies demonstrated enhanced liver imaging at 5 and 30 min. post injection with virtually no enhancement of the blood. Splenic retention was minimal and dissipated by 1 hour post injection. Kidney enhancement was noted at 30 minutes and 60 minutes post injection. The liver appeared to clear to the original x-ray density by 1 hour post injection.

EXAMPLE 8

Synthesis of WIN 16318

Ethyl 2-(3,5-bis(acetylamino-2,4,6-triiodobenzoyloxy)butyrate

To 500 mL of dry N,N-dimethylformamide was added 159 g (0.250 mol) sodium diatrizoate and 54.5 g (0.280 mol) of ethyl 2-bromobutyrate. The mixture was heated on a steam bath for 20 h, cooled to room temperature and poured into 3L of dilute ammonium hydroxide. The solid was filtered, washing with water, and air-dried. The solid was further purified by crystallization from 50% aqueous ethanol (after treatment with decolorizing carbon) affording two crops which were dried at 100° C. overnight to afford 121 g (66%) of a white powder, m.p. 288°-290° C. (dec.) . Analysis for $C_{17}H_{19}I_3N_2O_6$ calc'd/found C 28.05/28.36/H 2.63/2.55; I 52.3/52.3

In Vivo Imaging Studies Using Nanocrystalline WIN 16318; 10% WIN 16318, 2% Tween 80, 100 mM phosphate A nanoparticle suspension of WIN 16318 was prepared as described in Example 1 with the exception that only 6 g of WIN 16318 was added (i.e., 10% WIN 16318) and 1.2 g of a different surface modifier, i.e., Tween 80, was added (i.e., 2% Tween 80) and the liquid phase was made up of 100 mM phosphate buffer (pH=7.5). This was done to control the formulation pH and osmolality. These particles were characterized as described in Example 1. An average size of 219 nm was measured after 14 days of milling. The pH of the formulation was 7.8 and the osmolality was 348 mOsm/kg. Stability of this formulation was checked in fluids as described in Example 1 and demonstrated stability in PBS and rat plasma.

EXAMPLE 9

Lymphographic Imaging Using Nanocrystalline WIN 8883

A suspension prepared as described in Example 1 was used to image the lymph system (approximately 3 Kg rabbits) by computed tomography (CT). The suspension was dosed by percutaneous administration via the foot pads of the rabbits at 0.03 ml/Kg animal body weight and imaged 9 hours after administration. The CT images demonstrated enhanced x-ray contrast of the lymph nodes responsible for clearance from the anatomical areas of the rabbit injected with this formulation. Enhanced density was observed for times as long as 1 week after which the x-ray density of the lymph nodes returned to normal levels.

EXAMPLE 10

A formulation prepared as described in Example 3 having a particle size of 169 nm was imaged in rabbits at a dose of 3 ml/kg (100 mg/kg compound; 352 mgI/kg). Blood pool imaging at this dose was excellent up to at least 2 hours after compound administration.

The invention has been described in detail with particular reference to certain preferred embodiments thereof, but it will be understood that variations and modifications can be effected within the spirit and scope of the invention.

What is claimed is:

1. An x-ray contrast composition comprising particles consisting essentially of 99.9-10% by weight of a non-radioactive crystalline organic x-ray contrast agent having a solubility in water of less than 10 mg/ml, said x-ray contrast agent having a non-crosslinked surface modifier adsorbed on the surface thereof in an amount of 0.1-90% by weight and sufficient to maintain an effective average particle size of less than 400 nm, and a pharmaceutically acceptable carrier therefor.

2. The composition of claim 1 wherein said particles have an effective particle size of less than 300 nm.

3. The composition of claim 1 wherein said particles have an effective particle size of less than 200 nm.

4. The composition of claim 1 wherein said x-ray contrast agent is an iodinated aromatic compound.

5. The composition of claim 1 wherein said x-ray contrast agent is an ester or an amide of an iodinated aromatic acid selected from the group consisting of diatrizoic acid, metrizoic acid, iothalamic acid, trimesic acid and iodipamide.

6. The composition of claim 1 wherein said x-ray contrast agent is ethyl-3,5-diacetamido-2,4,6-triiodobenzoate.

7. The composition of claim 1 wherein said x-ray contrast agent is ethyl(3,5-bis(acetylamino)-2,4,6-triiodobenzoyloxy)acetate.

8. The composition of claim 1 wherein said x-ray contrast agent is ethyl-2-(3,5-bis(acetylamino)-2,4,6triiodobenzoyloxy)butyrate.

9. The composition of claim 1 wherein said carrier is water.

10. The composition of claim 1 wherein said particles are present in an amount of 10-25% by weight.

11. The composition of claim 1 wherein said surface modifier is a tetrafunctional block copolymer derived from sequential addition of propylene oxide and ethylene oxide to ethylenediamine.

12. The composition of claim 1 wherein said surface modifier has the formula

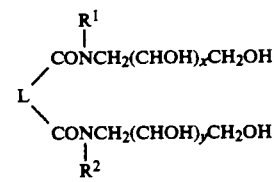

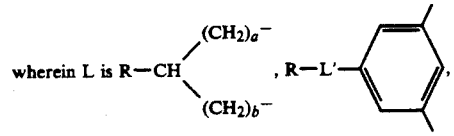

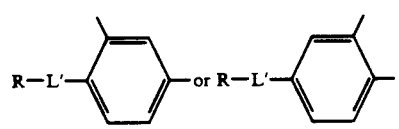

L' is a chemical bond, —O—, —S—, —NH—, —CONH— or —SO$_2$NH—;

R is a hydrophobic substituted or unsubstituted alkyl, substituted or unsubstituted cycloalkyl, or a substituted or unsubstituted aryl group;

each of $R^1$ and $R^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

13. The x-ray contrast composition of claim 1 wherein said particles consist essentially of crystalline ethyl-3,5-diacetamido-2,4,6-triiodobenzoate having a tetrafunctional block copolymer derived from sequential addition of ethylene oxide and propylene oxide to ethylenediamine adsorbed on the surface thereof.

14. The x-ray contrast composition of claim 1 wherein said particles consist essentially of crystals of the ethyl glycolate ester of diatrizoic acid having a tetrafunctional block copolymer derived from sequential addition of ethylene oxide and propylene oxide to ethylenediamine adsorbed on the surface thereof.

15. The x-ray contrast composition of claim 1 wherein said particles consist essentially of crystalline ethyl-2-(3,5-bis(acetylamino)-2,4,6-triiodobenzoyloxy)-butyrate having a tetrafunctional block copolymer derived from sequential addition of ethylene oxide and propylene oxide to ethylenediamine adsorbed on the surface thereof.

16. A method for medical x-ray diagnostic imaging which comprises administering to the body of a test subject an effective contrast producing amount of the x-ray contrast composition defined in claim 1.

17. The method of claim 16 wherein said surface modifier is present in an amount of 10 to 30% by weight based on the total weight of the dry particle.

18. The x-ray contrast composition of claim 1 wherein said surface modifier is a surfactant.

19. The x-ray contrast compositon of claim 1 wherein said surface modifier is a nonionic surfactant.

20. The x-ray contrast compositon of claim 1 wherein said surface modifier is a anionic surfactant.

21. The x-ray contrast composition of claim 1 wherein said surface modifier is selected from the group consisting of gelatin, casein, gum acacia, cholesterol, tragacanth, stearic acid, benzalkonium chloride, calcium stearate, glyceryl monostearate, cetostearyl alcohol, cetamacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, caboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, poloxomers, poloxamines, dextran, a dioctyl ester of sodium sulfosuccinic acid, sodium lauryl sulfate, and an alkyl aryl polyether sulfonate.

22. The x-ray contrast composition of claim 1 wherein said surface modifier is present in an amount of 10 to 60% by weight based on the total weight of the dry particle.

23. The x-ray contrast composition of claim 1 wherein said surface modifier is present in an amount of 10 to 30% by weight based on the total weight of the dry particle.

24. The method of claim 16 wherein said surface modifier is a surfactant.

25. The method of claim 16 wherein said surface modifier is a nonionic surfactant.

26. The method of claim 16 wherein said surface modifier is an anionic surfactant.

27. The method of claim 16 wherein said surface modifier is selected from the group consisting of gelatin, casein, gum acacia, cholesterol, tragacanth, stearic acid, benzalkonium chloride, calcium stearate, glyceryl monostearate, cetostearyl alcohol, cetamacrogol emulsifying wax, sorbitan esters, polyoxyethylene alkyl ethers, polyoxyethylene caster oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, poloxomers, poloxamines, dextran, a dioctyl ester of sodium sulfosuccinic acid, sodium lauryl sulfate and an alkyl aryl polyether sulfonate.

28. The method of claim 16 wherein said surface modifier is present in an amount of 10 to 60% by weight based on the total weight of the dry particle.

* * * * *